United States Patent
Auld et al.

(10) Patent No.: US 7,470,269 B2
(45) Date of Patent: Dec. 30, 2008

(54) OPHTHALMIC SURGERY LIGHT TRANSMITTING APPARATUS

(75) Inventors: Michael D. Auld, Chesterfield, MO (US); Michael S. Poulsen, House Springs, MO (US)

(73) Assignee: Synergetics, Inc., O'Fallon, MO (US)

( * ) Notice: Subject to any disclaimer, the term of this patent is extended or adjusted under 35 U.S.C. 154(b) by 807 days.

(21) Appl. No.: 10/435,100

(22) Filed: May 9, 2003

(65) Prior Publication Data

US 2004/0010247 A1   Jan. 15, 2004

Related U.S. Application Data

(60) Provisional application No. 60/394,945, filed on Jul. 10, 2002.

(51) Int. Cl.
*A61B 18/20* (2006.01)
*A61F 9/008* (2006.01)

(52) U.S. Cl. .................... 606/4; 606/15; 606/16

(58) Field of Classification Search .............. 606/4, 606/7–16
See application file for complete search history.

(56) References Cited

U.S. PATENT DOCUMENTS

| 4,583,539 | A | * | 4/1986 | Karlin et al. ............. 606/4 |
| 4,729,621 | A | * | 3/1988 | Edelman .................. 606/15 |
| 4,911,711 | A | * | 3/1990 | Telfair et al. ............ 606/5 |
| 5,470,330 | A | * | 11/1995 | Goldenberg et al. ...... 606/10 |
| 5,738,677 | A | * | 4/1998 | Colvard et al. .......... 606/4 |

FOREIGN PATENT DOCUMENTS

WO         9102562       *   3/1991    ............ 606/15

* cited by examiner

*Primary Examiner*—David Shay
(74) *Attorney, Agent, or Firm*—Thompson Coburn LLP

(57) ABSTRACT

An ophthalmic surgery light transmitting apparatus has an optic fiber having a flexible length with a light source connector mounted on one end of the optic fiber and the opposite end of the optic fiber being adapted to be mounted to an ophthalmic surgery instrument to provide illumination for the instrument. The cross-sectional area of the optic fiber transitions as it extends from the end connected to the light source connector to the opposite end of the optic fiber. The optic fiber transitions from a larger cross-sectional area of the optic fiber at the light source connector to a smaller cross-sectional area of the optic fiber at the opposite end.

18 Claims, 2 Drawing Sheets

US 7,470,269 B2

OPHTHALMIC SURGERY LIGHT TRANSMITTING APPARATUS

CROSS REFERENCE TO RELATED APPLICATIONS

Figure 1:
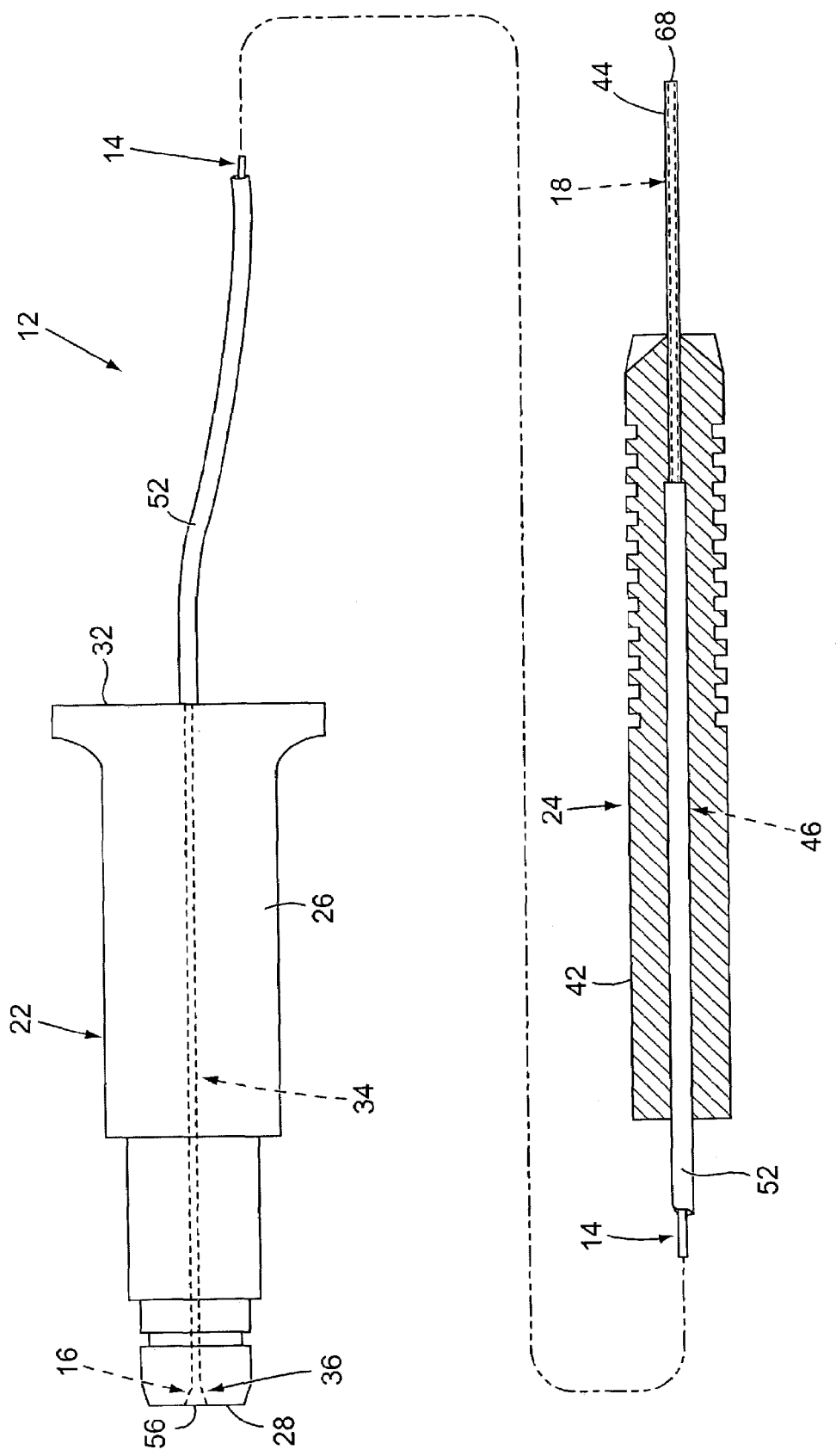

This application claims the benefit of provisional Patent Application No. 60/394,945, titled Ophthalmic Surgery Light Pipe, filed Jul. 10, 2002.

BACKGROUND OF THE INVENTION (1) Field of the Invention

The present invention pertains to a light transmitting apparatus that is employed primarily in ophthalmic surgery. The apparatus is comprised of an optic fiber having a flexible length with a light source connector mounted on one end of the optic fiber. The opposite end of the optic fiber is adapted to be mounted on an ophthalmic surgery instrument to serve as a source of illumination for the instrument. The cross-sectional area of the optic fiber transitions as it extends from its proximal end to its distal end, with the cross-sectional area adjacent the optic fiber proximal end being larger than the cross-sectional area adjacent the optic fiber distal end. The changes in the cross-sectional area of the optic fiber along its length enable the optic fiber to transmit a greater amount of light from its proximal end to its distal end than was previously possible with prior art light transmitting optic fibers having a constant cross-sectional area along their lengths.

(2) Description of the Related Art

In a typical ophthalmic surgery procedure, it is necessary that a light source be provided inside the patient's eye so that the surgical site in the interior of the eye is well illuminated, enabling the surgeon to easily view the surgical site through an endoscope. Most common ophthalmic surgery procedures involve first making a small incision in the eye for insertion of an illuminator. A second incision is made in the eye for insertion of the instrument to be used by the surgeon in performing the surgery. Alternatively, when using an instrument that is provided with its own light source, only a single incision is made in the eye for insertion of the illuminated instrument into the interior of the eye. To minimize the invasiveness of this type of surgery, it is desirable to reduce the size of the incisions. This is accomplished by reducing the sizes of the light source or illuminated instruments inserted through the incisions.

There are various different types of illumination devices employed in ophthalmic surgery. These include illumination cannulas that are inserted through an incision in the eye and secured to the exterior surface of the eye. One or more optic fibers extends through the cannula. The proximal end of each optic fiber is typically secured to a connector that connects to a light source. The distal end of each optic fiber is positioned in the cannula where, when the connector is connected to the light source, light transmitted through the optic fiber is emitted from the distal end of the optic fiber illuminating the interior of the eye. An example of this type of illumination device is disclosed in U.S. Pat. No. 5,425,730.

Other types of illumination devices are incorporated into microsurgical instruments employed in ophthalmic surgery. These types of illumination devices also typically employ one or more optic fibers having flexible lengths with opposite proximal and distal ends. The proximal end of each fiber is again secured to a connector that connects the fiber proximal end to a light source. The distal end of each fiber is adapted to be mounted to an ophthalmic surgery instrument, for example a pick or blade, a scissors or a forceps. Connecting the connector to a light source transmits light through the optic fiber to the optic fiber distal end providing illumination to the area of the working end of the ophthalmic surgery instrument. Examples of these types of instruments are disclosed in U.S. Pat. Nos. 5,785,645 and 5,807,242.

The miniaturization of ophthalmic surgery instruments that provide illumination to a surgical site in the eye has resulted in a reduction in the size of the instrument's optic fiber which has resulted in a reduction in the capability of the optic fiber to introduce enough light to the surgical site for effective visualization by the surgeon. As explained above, the typical illuminated ophthalmic surgery instrument employs at least one optic fiber having a flexible length with opposite proximal and distal ends. The proximal end of the fiber is attached to a light source connector and the distal end of the fiber is attached to an ophthalmic surgery instrument or is adapted to be attached to an instrument. The typical optic fiber employed with ophthalmic surgery instruments has a diameter of 0.75 mm. Reducing the size of the ophthalmic surgery instrument to enable a reduction in the size of the incision in the eye requires a corresponding reduction in the diameter of the optic fiber of the instrument. However, the amount of illumination that can be transmitted by an optic fiber is fundamentally dependent on the cross-sectional area of the optic fiber. A reduction in the cross-sectional area of the optic fiber reduces its ability to transmit illuminating light to the surgical site. Therefore, there is a need for a light transmitting apparatus employed with ophthalmic surgery instruments that has a reduced size, enabling a reduction in the size of an incision into the eye and a reduction in the invasiveness of ophthalmic surgery, while still transmitting sufficient light to the interior of the eye for effective illumination and visualization of the surgical site by the surgeon.

SUMMARY OF THE INVENTION

The present invention pertains to a light transmitting apparatus that is comprised of a length of optic fiber having opposite proximal and distal ends with a light source connector at the optic fiber proximal end and with the optic fiber distal end being adapted to be mounted on an ophthalmic surgery instrument.

The light source connector is similar to prior art light source connectors. It is comprised of a cylindrical, metal body having opposite proximal and distal ends. The proximal end of the connector body is designed to be removably secured to a commercially available light source. A center bore extends through the connector body between its proximal and distal ends. However, the connector differs from prior art light source connectors in that a portion of the center bore adjacent the body proximal end has a conical interior surface.

The optic fiber has a flexible length with opposite proximal and distal ends. A flexible, protective sheath extends over the optic fiber for a majority of its length. A portion of the sheath is removed adjacent the proximal end of the optic fiber exposing a portion of the optic fiber adjacent the proximal end. A portion of the sheath is also removed adjacent the distal end of the optic fiber exposing a portion of the optic fiber adjacent the distal end.

The optic fiber differs from optic fibers of the prior art in that the cross-sectional area of the optic fiber changes as it extends from the proximal end of the optic fiber to the distal end of the optic fiber. A first cross-sectional area of the optic fiber at the optic fiber proximal end is enlarged and has the largest cross-sectional area of the optic fiber. As the optic fiber extends from its proximal end toward its distal end, the optic fiber extends through a first tapered section where the optic fiber tapers downwardly to a portion of the optic fiber having a second cross-sectional area. The tapering of the optic fiber adjacent the optic fiber proximal end is shaped complementary to the conical interior surface of the bore of the light source connector.

A majority of the length of the optic fiber between the optic fiber proximal end and distal end has the second cross-sectional area. As the optic fiber approaches the distal end it extends through a second tapered section where the optic fiber tapers downwardly from the portion of the optic fiber having the second cross-sectional area to a portion of the optic fiber having a third cross-sectional area. The portion of the optic fiber length having the third cross-sectional area is adapted to be mounted on an ophthalmic surgery instrument to provide illumination to the working end of the instrument.

With the proximal end of the optic fiber having an enlarged cross-sectional area that is larger than the cross-sectional area of a typical ophthalmic surgery instrument, the proximal end of the optic fiber can receive a greater amount of incident light from the light source than can the prior art optic fiber. This results in a greater amount of light being received and transmitted by the optic fiber of the invention than is possible with prior art optic fibers having smaller cross-sectional areas at their proximal end surfaces. As the light is transmitted through the length of the optic fiber it passes through the first tapered section and the second tapered section of the optic fiber to the portion of the optic fiber adjacent the distal end having the third cross-sectional area. The third cross-sectional area of the optic fiber adjacent the optic fiber distal end is smaller than the cross-sectional area of the distal end or light emitting end of a typical optic fiber employed with prior art ophthalmic surgery instruments. However, although the third cross-sectional area of the distal end of the optic fiber is smaller than that of prior art optic fibers, because the proximal end of the optic fiber receives a greater amount of incident light, the illumination provided by the distal end of the optic fiber is greater than that provided by prior art optic fibers having a larger cross-sectional area.

In the preferred embodiment of the light transmitting apparatus of the invention, the proximal end of the optic fiber is enlarged by subjecting the proximal end to heat which causes the optic fiber proximal end to expand. The cross-sectional area of the portion of the optic fiber adjacent the optic fiber distal end is reduced in cross-sectional area by subjecting this portion of the optic fiber to heat while drawing out or stretching the portion of the optic fiber. This results in the portion of the optic fiber adjacent the distal end being reduced in cross-sectional area from that of the typical prior art optic fiber.

Thus, the light transmitting apparatus of the invention provides an optic fiber that has a reduced size adjacent its distal end enabling a reduction in the size of an incision in the eye through which the distal end portion of the optic fiber is inserted. This provides a light transmitting apparatus that is less invasive than prior art light transmitting apparatus. Still further, the increased size of the optic fiber at its proximal end enables the optic fiber of the invention to transmit a greater amount of light than is possible with the typical optic fiber employed with ophthalmic surgery instruments.

BRIEF DESCRIPTION OF THE DRAWING FIGURES

Figure 2:
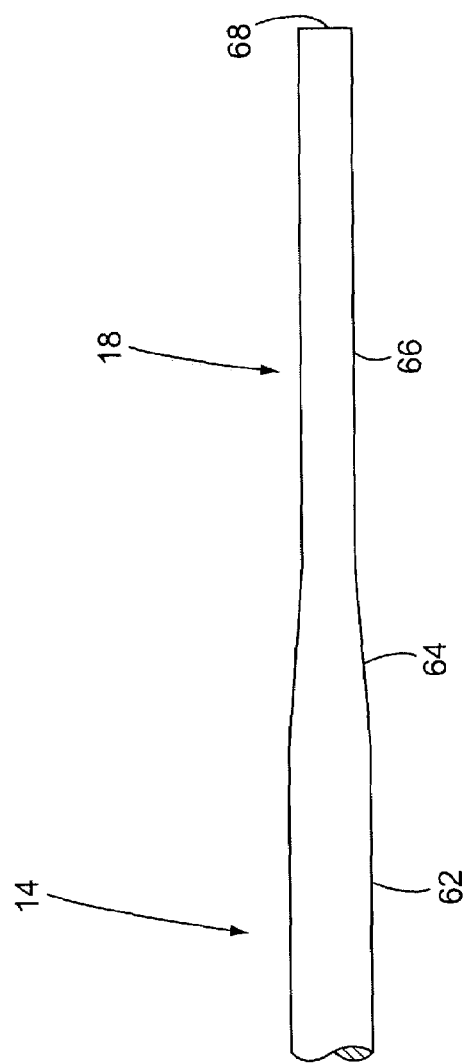
Figure 2:
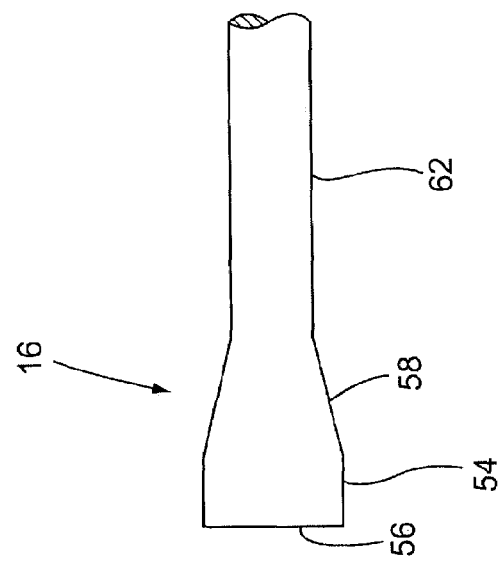

Further features of the invention are set forth in the following detailed description of the preferred embodiment of the invention and in the drawing figures wherein:

FIG. 1 shows a cross-sectioned, fragmented view of the light transmitting apparatus of the invention; and FIG. 2 shows an enlarged, fragmented view of the optic fiber removed from the apparatus of the invention of FIG. 1.

DETAILED DESCRIPTION OF A PREFERRED EMBODIMENT

FIG. 1 shows the ophthalmic surgery light transmitting apparatus 12 of the present invention. The apparatus 12 is basically comprised of a length of optic fiber 14 having opposite proximal 16 and distal 18 ends with a light source connector 22 at the optic fiber proximal end and an ophthalmic surgery instrument 24 at the fiber distal end. The ophthalmic surgery instrument 24 could be permanently secured to the optic fiber distal end 18. Alternatively, the optic fiber distal end 18 could be adapted to be removably inserted into any one of various different types of ophthalmic surgery instruments.

As stated earlier, the light source connector 22 is similar in construction to prior art light source connectors employed with light transmitting ophthalmic surgery instruments. The connector has a cylindrical, metal body 26 having opposite proximal 28 and distal 32 ends. The exterior configuration of the connector body 26 is determined depending on the particular commercially available light source with which the apparatus 12 is to be used. Different manufacturers of light sources for ophthalmic surgery instruments often also manufacture their own surgical instruments. These manufacturers will provide the light source connectors on their surgical instruments with a particular configuration that enables the connector to be easily attached and removed from their light source. Therefore, the particular exterior configuration of the light source connector 22 shown in the drawing figures is illustrative only. The light transmitting apparatus 12 of the invention that is used with different types of light sources will have a light source connector 22 with an exterior configuration that is adapted to removably attach the connector to the particular light source.

The light source connector 22 has a center bore 34 that extends completely through the connector and intersects the opposite proximal end surface 28 and distal end surface 32 of the connector. A majority of the length of the center bore 34 is dimensioned to receive the proximal end 16 of the optic fiber 14 in a manner to be explained. However, a portion of the center bore 36 adjacent the proximal end surface 28 of the connector has a conical or tapered interior surface. As this portion of the center bore 36 extends from the light source connector proximal end surface 28 toward the light source connector distal end surface 32, it tapers downwardly and reduces in cross-sectional area until it intersects with the remainder of the center bore 34 having a constant cross-sectional area.

The ophthalmic surgery instrument 24 shown in FIG. 1 is only one example of an ophthalmic surgery instrument with which the light transmitting apparatus 12 of the invention may be employed. The instrument 24 is shown for illustrative purposes only and the light transmitting apparatus 12 of the invention may be employed with other types of instruments such as the illumination cannula described earlier or an ophthalmic surgery pick or blade, a scissors or a forceps. The light transmitting apparatus 12 of the invention is not intended to be limited to use with any one particular type of ophthalmic surgery instrument. Furthermore, an ophthalmic surgery instrument could be permanently attached to the distal end 18 of the optic fiber of the apparatus, or could be removably attached to the distal end enabling the light transmitting apparatus 12 to be removably attached to various different types of ophthalmic surgery instruments.

The ophthalmic surgery instrument 24 shown is a light pipe and is comprised of an instrument handle 42 and a tubular needle 44 projecting from the handle. The instrument has a center bore 46 that extends through the handle 42 and the needle 44. The tubular needle 44 is a metal 25-gauge (0.50 mm) diameter needle. This is smaller than the typical 20-guage (0.89 mm) needle employed on prior art light picks. The smaller diameter needle 44 of the light pick enables a smaller, less invasive incision into the eye in using the instrument. The smaller diameter needle 44 is enabled by a smaller cross-section portion of the light transmitting apparatus 12 to be described.

The optic fiber 14 of the light transmitting apparatus 12 is a 25-guage (0.50 mm) diameter optic fiber that has been modified for the apparatus 12 of the invention. The optic fiber 14 is shown fragmented in FIGS. 1 and 2. The optic fiber 14 has a length between its opposite proximal 16 and distal 18 ends that is sufficiently long to enable the surgeon to freely manipulate the optic fiber distal end 18 that is mounted to a surgical instrument with the optic fiber proximal end 16 secured stationary to a light source by the light source connector 22. The optic fiber 14 is freely flexible along its length. A protective sheath 52 extends over the optic fiber for a majority of its length. A portion of the sheath 52 is removed from the optic fiber exposing a portion of the optic fiber adjacent its proximal end 16. A portion of the sheath 52 is also removed from the optic fiber 14 exposing a portion of the optic fiber adjacent the distal end 18. As shown in FIG. 1, the exposed portion of the optic fiber 14 adjacent the optic fiber proximal end 16 is inserted into the center bore 34 of the light source connector 22. The exposed portion of the optic fiber 14 adjacent the optic fiber distal end 18 is inserted into the center bore 46 of the surgical instrument handle 42 and needle 44.

FIG. 3 shows an enlarged, fragmented view of the optic fiber 14 removed from the sheath 52, the light source connector 22, and the ophthalmic surgery instrument 24. The optic fiber 14 differs from optic fibers of the prior art in that the cross-sectional area of the optic fiber changes as it extends from the proximal end 16 of the optic fiber to the distal end 18 of the optic fiber. A first proximal end portion 54 of the optic fiber has a first cross-sectional area that is the largest cross-sectional area of the optic fiber along its entire length. This proximal end portion 54 of the optic fiber has had its diameter increased from the original 0.50 mm diameter by heating which causes the optic fiber to expand. The heating and expansion of the proximal end portion 54 of the optic fiber is controlled so that the fiber proximal end assumes the configuration of the conical entry portion 36 of the light source connector center bore 34. This can be accomplished by positioning the proximal end portion 54 of the fiber inside the light source connector center bore 34 and then heating the optic fiber proximal end portion 54. The expansion of the optic fiber proximal end portion 54 resulting from the heating will conform to the interior surface of the conical center bore portion 36 of the light source connector 22. Alternatively, a mold could be provided to mold the optic fiber proximal end portion 54 into a conical configuration that is complementary to the conical configuration of the center bore portion 36 of the light source connector 22. The proximal end portion 54 of the optic fiber has had its cross-sectional area increased by increasing its diameter to 0.70 mm from the 0.50 mm diameter of the majority of the length of the optic fiber 14. With the optic fiber proximal end portion 54 positioned in the center bore 34 of the light source connector 22, a proximal end surface 56 of the optic fiber 14 is cut and polished flush with the proximal surface 28 of the light source connector 22. The optic fiber proximal end surface 56 has a first cross-sectional area of the optic fiber.

As the optic fiber 14 extends from its proximal end surface 56 toward the distal end 18 of the optic fiber, the optic fiber extends through a first tapered section 58 where the optic fiber tapers downwardly from its expanded diameter of 0.70 mm to an intermediate portion of the optic fiber length 62 having the 0.50 mm diameter. This intermediate portion 62 of the optic fiber extends along a majority of the length of the optic fiber and has a second cross-sectional area that is smaller than the first cross-sectional area of the optic fiber. The first tapered section 58 of the optic fiber is shaped complementary to the conical interior surface portion 36 of the light source connector interior bore 34.

The majority of the length of the optic fiber 14 between the optic fiber proximal end 16 and the optic fiber distal end 18 has the second cross-sectional area and a diameter of 0.50 mm. As the optic fiber 14 extends along the intermediate portion 62 toward the optic fiber distal end 18 it extends through a second tapered section 64. Here the optic fiber tapers downwardly from the intermediate portion 62 of the optic fiber having the second cross-sectional area and a diameter or 0.50 mm, to a distal end portion 66 of the optic fiber having a third cross-sectional area and a diameter of 0.40 mm. The optic fiber second tapered section 64 is positioned in the center bore 46 of the instrument just before the center bore 64 enters the needle 44. The distal end portion of the optic fiber 66 having a diameter of 0.40 mm is reduced in size sufficiently to be inserted through a 25-guage needle having a diameter of 0.50 mm. The reduction in the cross-sectional area and diameter of the distal end portion 66 of the optic fiber is achieved by heating the distal end portion 66 and drawing out or stretching the distal end portion by tension. A distal end surface 68 of the optic fiber 14 is cut and polished to enhance light emission from the distal end surface.

In one embodiment of the light transmitting apparatus 16, the distal end portion 66 of the optic fiber is left with the bare fiber projecting from the sheath 52. The bear fiber of the distal end portion 66 can be removably mounted to a variety of different ophthalmic surgery instruments.

Alternatively, the distal end portion 66 of the optic fiber can be inserted into a center bore of an ophthalmic surgery instrument, for example the center bore 46 of the instrument 24 shown in FIG. 1, and permanently secured in place by adhesives or other equivalent means.

With the proximal end surface 56 of the optic fiber having an enlarged cross-sectional area that is larger than the cross-sectional area of a typical ophthalmic surgery instrument, the proximal end surface 56 can receive a greater amount of incident light from the light source than can the prior art optic fiber. This results in a greater amount of light being received and transmitted by the light transmitting apparatus 12 than is possible with prior art optic fibers having smaller cross-sectional areas at their proximal end surfaces. As the light is transmitted through the length of the optic fiber 14 it passes through the first tapered section 58 and the second tapered section 64 to the distal end portion 66 of the optic fiber having the third cross-sectional area and a diameter of 0.40 mm. The distal end portion 66 of the optic fiber has a cross-sectional area and a diameter that are smaller than the cross-sectional area and diameter of the distal end or light emitting end of a typical optic fiber employed with prior art ophthalmic surgery instruments. However, although the distal end portion 66 of the optic fiber has a smaller cross-sectional area than that of prior art optic fibers, because the proximal end portion 54 of the optic fiber receives a greater amount of incident light, the illumination provided by the distal end portion 66 of the optic fiber is greater than that provided by prior art optic fibers having a larger cross-sectional area.

Thus, the light transmitting apparatus 12 of the invention provides an optic fiber that has a reduced cross-sectional area and diameter adjacent its distal end which enables a reduction in the size of an incision in the eye through which the distal end portion of the optic fiber is inserted. This provides a light transmitting apparatus that is less invasive than prior art light transmitting apparatus. Still further, the increased size of the optic fiber at its proximal end enables the optic fiber of the invention to transmit a greater amount of light than is possible with the typical optic fiber employed with prior art ophthalmic surgery instruments.

While the present invention has been described by reference to a particular embodiment, it should be understood that modifications and variations of the invention may be constructed without departing from the scope of the invention defined in the following claims.

What is claimed is:

1. A surgery light transmitting apparatus comprising:
an optic fiber having a length between opposite proximal and distal end surfaces, the optic fiber length having a proximal portion adjacent the optic fiber proximal end surface that has a first cross-sectional area, the optic fiber length having an intermediate portion adjacent the proximal portion that has a second cross-sectional area that is smaller than the first cross-sectional area, the optic fiber length having a distal portion adjacent the optic fiber distal end surface that has a third cross-sectional area that is smaller than the second cross-sectional area, where the intermediate portion of the optic fiber length extends along a majority of the optic fiber length between the proximal and distal end surfaces; and,
the first-cross-sectional area being constant along the proximal portion of the optic fiber length, the second cross-sectional area being constant along the intermediate portion of the optic fiber length, and the third cross-sectional area being constant along the distal portion of the optic fiber length.

2. The apparatus of claim 1, further comprising:
the optic fiber length having a first tapered section between the proximal portion and the intermediate portion of the optic fiber length where the optic fiber tapers down from the first cross-sectional area to the second cross-sectional area, and a second tapered section between the intermediate portion and the distal portion of the optic fiber length where the optic fiber tapers down from the second cross-sectional area to the third cross-sectional area.

3. The apparatus of claim 2, further comprising:
the optic fiber length between the proximal end surface and the distal end surface consisting essentially of the proximal portion, the first tapered section, the intermediate portion, the second tapered section, and the distal portion of the optic fiber length.

4. The apparatus of claim 1, further comprising:
a light source connector mounted on the optic fiber proximal portion; and,
a surgical instrument mounted on the optic fiber distal portion.

5. The apparatus of claim 4, further comprising:
the intermediate portion of the optic fiber length extending between the light source connector and the surgical instrument.

6. The apparatus of claim 4, further comprising:
the surgical instrument having a handle and a tubular needle projecting from the handle, and the distal portion of the optic fiber length extending through the tubular needle.

7. The apparatus of claim 6, further comprising:
the third cross-sectional area being constant along the distal portion of the optic fiber length extending through the tubular needle.

8. The apparatus of claim 6, further comprising:
the distal portion of the optic fiber length being removably mounted in the tubular needle.

9. A surgery light transmitting apparatus comprising:
an optic fiber having a length between opposite proximal and distal end surfaces, the optic fiber length having a proximal portion adjacent the proximal end surface that has a first cross-sectional area, the optic fiber length having an intermediate portion adjacent the proximal portion that has a second cross-sectional area that is smaller than the first cross-sectional area, the optic fiber length having a distal portion adjacent the optic fiber distal end surface that has a third cross-sectional area that is smaller than the second cross-sectional area;
a light source connector mounted on the optic fiber proximal portion;
a surgical instrument mounted on the optic fiber distal portion, the surgical instrument having a tubular needle and the distal portion of the optic fiber extending through the tubular needle to the distal end surface of the optic fiber; and,
the optic fiber length having a first tapered section between the proximal portion and the intermediate portion of the optic fiber length where the optic fiber tapers down from the first cross-sectional area to the second cross-sectional area, and a second tapered section between the intermediate portion and the distal portion of the optic fiber length where the optic fiber tapers down from the second cross-sectional area to the third cross-sectional area.

10. The apparatus of claim 9, further comprising:
the optic fiber length between the proximal end surface and the distal end surface consisting essentially of the proximal portion, the first tapered section, the intermediate portion, the second tapered section, and the distal portion of the optic fiber length.

11. The apparatus of claim 9, further comprising:
the first-cross-sectional area being constant along the proximal portion of the optic fiber length, the second cross-sectional area being constant along the intermediate portion of the optic fiber length, and the third cross-sectional area being constant along the distal portion of the optic fiber length.

12. The apparatus of claim 9, further comprising:
the optic fiber second tapered section being outside the needle.

13. The apparatus of claim 9, further comprising:
the optic fiber first tapered section being inside the light source connector.

14. The apparatus of claim 9, further comprising:
the intermediate portion of the optic fiber length extending between the light source connector and the surgical instrument.

15. The apparatus of claim 9, further comprising:
the optic fiber distal portion having a constant cross-sectional area extending through the instrument needle.

16. The apparatus of claim 15, further comprising:
the surgical instrument having a handle, and the needle being rigid and projecting from the handle.

17. The apparatus of claim 15, further comprising:
the intermediate portion of the optic fiber length extending into the instrument and the distal portion of the optic fiber length extending into the needle.

18. A surgery light transmitting apparatus comprising:
an optic fiber having a length between opposite proximal and distal end surfaces, the optic fiber length having a proximal portion adjacent the proximal end surface that has a first cross-sectional area, the optic fiber length having an intermediate portion adjacent the proximal portion that has a second cross-sectional area that is smaller than the first cross-sectional area, the optic fiber length having a distal portion adjacent the optic fiber distal end surface that has a third cross-sectional area that is smaller than the second cross-sectional area;

a light source connector mounted on the optic fiber proximal portion;

a surgical instrument mounted on the optic fiber distal portion, the surgical instrument having a tubular needle and the distal portion of the optic fiber extending through the tubular needle to the distal end surface of the optic fiber; and, the tubular needle having an end and the optic fiber distal end surface being at the needle end.

\* \* \* \* \*